(12) United States Patent
Haskins et al.

(10) Patent No.: US 7,794,971 B1
(45) Date of Patent: Sep. 14, 2010

(54) COMPOSITIONS AND METHODS FOR CONTROLLING COPY NUMBER FOR A BROAD RANGE OF PLASMIDS AND USES THEREOF

(75) Inventors: Darin J. Haskins, Blue Mound, WI (US); Leslie M. Hoffman, Madison, WI (US)

(73) Assignee: Epicentre Technologies Corporation, Madison, WI (US)

( * ) Notice: Subject to any disclaimer, the term of this patent is extended or adjusted under 35 U.S.C. 154(b) by 145 days.

(21) Appl. No.: 10/883,459

(22) Filed: Jul. 1, 2004

Related U.S. Application Data

(60) Provisional application No. 60/483,955, filed on Jul. 1, 2003.

(51) Int. Cl.
*C12N 15/00* (2006.01)
*C12N 15/85* (2006.01)
(52) U.S. Cl. ..................... 435/69.1; 435/325
(58) Field of Classification Search ............ None
See application file for complete search history.

(56) References Cited

U.S. PATENT DOCUMENTS

| | | | |
|---|---|---|---|
| 4,487,835 | A | 12/1984 | Uhlin |
| 4,495,287 | A | 1/1985 | Uhlin |
| 4,499,189 | A | 2/1985 | Uhlin |
| 5,015,573 | A | 5/1991 | Yarranton |
| 5,874,259 | A | 2/1999 | Szybalski |
| 6,165,749 | A | 12/2000 | Sagawa |
| 6,472,177 | B1 | 10/2002 | Szybalski |

OTHER PUBLICATIONS

Studier et al. J. Mol. Biol. 189(1): 113-130, 1986.*
Xu et al. Polyadenylation can regulate ColE1 type plasmid copy number independently of any effect on RNAI decay by decreasing the interaction of antisense RNAI with its RNAII target. Plasmid. Jul. 2002;48(1):49-58.*
Actis, L. et al. Frontiers in Bioscience, 3: d43-62 (1998).
Binnie, U., et al. Microbiology 145 ( Pt 11):3089-100 (Nov. 1999).
Binns, N. and M. Masters, Mol. Microbiol., 44: 1287-1298, (2002).
Blomberg P, et al., Embo J. 9(7):2331-40. (Jul. 1990).
Bolivar, F., Life Sci. 3:25(10): 807-17 (Sep. 1979).
Brantl, S. Plasmid., 48(3):165-73 (Nov. 2002).
Cao, GJ, Sarkar, N., Proc Natl Acad Sci U S A. 1;89(21):10380-4 (Nov. 1992).
Cao, GJ, et al. Proc Natl Acad Sci U S A. 15;93(21):11580-5. (Oct. 1996).
Covarrubias, L, et al. Gene 13(1):25-35 (Jan.-Feb. 1981).
Del Solar, G. and Espinosa, M. Molecular Microbiol., 37: 492-500, 2000.
Del Solar, G. et al. Microbiology and Molecular Biology Reviews, 62: 434-464, 1998.
Dery, KJ, et al. Plasmid 38(2):97-105 (1997).
Eguchi, Y., et al., Annu. Rev. Biochem., 60: 631-652, 1991.
Fu, J.F., et al., Plasmid 34(2):75-84 (Sep. 1995 ).
Hajnsforf, E., and Regnier, P.,J Mol Biol. 5;286(4):1033-43 (Mar. 1999).and.
Hamilton, C.M, Gene 24;200(1-2):107-16 (Oct. 1997).
Ingle, C.A. and Kushner, S.R., Proc Natl Acad Sci U S A. 12;93(23):12926-31 (Nov. 1996).
Jasiecki, J, and Wegrzyn, G., EMBO Rep.;4(2):172-7 (Feb. 2003).
Li, Z, et al., Proc Natl Acad Sci U S A. 13;95(21):12158-62. (Oct. 1998).
Liu, J.D, and Parkinson, J.S., J Bacteriol. 171(3):1254-1261 (Mar. 1989).
Lutz, R., Bujard, H. Nucleic Acids Res., 25: 1203-1210, 1997.
Malmgren, C., et al., RNA 2(10):1022-32 (Oct. 1996).
Marians, K.J., Annu Rev Biochem. 61:673-719 (1992).
Masters, M, et al., J Bacteriol. 175(14):4405-13 (Jul. 1993).
Mohanty, B. K. and Kushner, S. R.., Mol Microbiol. 34(5):1094-108 (Dec. 1999).
Nordstrom, K, et al., Gene 10;72(1-2):237-40 (Dec. 1988).
Raynal, L.C. and Carpousis, A.J. Mol Microbiol. 32(4):765-75 (May 1999).
Soderholm, F., Wagner, E.G., Microbiology. 144 ( Pt 7):1907-17 (Jul. 1998).
Stougaard, P., et al., Proc Natl Acad Sci U S A. 78(10):6008-12 (Oct. 1981).
Studier, F. et al., Methods Enzymol., 185: 60-89, 1990.
Vieria, J, and Messing, J., Gene 19(3):259-68 (Oct. 1982).
Wagner, E. G, Simons, R.W. Annu Rev Microbiol. 48:713-42. (1994).
Xu, F., Cohen, S.N., Nature Mar. 9, 1995;374(6518):180-3 (Mar. 1995).
Xu, F., et al., Plasmid 48(1):49-58( Jul. 2002).
Xu, F, et al., Proc Natl Acad Sci U S A. 90(14):6756-60 (Jul. 15, 1993).
Yehudai-Resheff, S., Schuster, G., Nucleic Acids Res. 28(5):1139-44 (Mar. 1, 2000).
Malmgren, C. J. Biol. Chem. 9:272(19):12508-12 (May 1997).
Bhagwat, A.S., Person, S., Mol Gen Genet. 182(3):505-7 (1981).
Blomberg, P, et al. Embo J. 11(7):2675-83 (Jul. 1992).
Blomberg, P,et al., Mol Microbial., 12(1):49-60 (Apr. 1994).
Lopilato, J., et al., Mol Gen Genet.;205(2):285-290 (Nov. 1986).
Malmgren, C., et al., J Biol Chem. 9;272(19):12508-12 (May 1997).
Masters, M., et al., Mol Gen Genet. 220(2):341-344 (Jan. 1990).
Raynal, L.C., et al., Biochimie. 78(6):390-8 (1996).
Sarkar, N., Microbiology 142 ( Pt 11):3125-33 (Nov. 1996).
Soderbom, F., et al., Mol Microbiol. 26(3):493-504 (Nov. 1997).
Wagner, E., et al., Embo J., 11: 1195-1203 (1992).

* cited by examiner

*Primary Examiner*—Michele K Joike
(74) *Attorney, Agent, or Firm*—Quarles & Brady LLP

(57) ABSTRACT

The present invention provides compositions and methods for controlling the copy number for a broad range of plasmids and uses thereof. Disclosed is a host cell for conditional control of copy number of a plasmid, which host cell comprises a poly(A) polymerase gene that is operably joined to a conditionally inducible promoter, and a method for cloning and stably maintaining a DNA sequence encoding a heterologous polypeptide in the host cell.

3 Claims, 1 Drawing Sheet

COMPOSITIONS AND METHODS FOR CONTROLLING COPY NUMBER FOR A BROAD RANGE OF PLASMIDS AND USES THEREOF

CROSS-REFERENCE TO RELATED APPLICATION

This application claims priority to U.S. Provisional Patent Application Ser. No. 60/483,955, filed Jul. 1, 2003. The entire disclosure of all priority applications is specifically incorporated herein by reference.

STATEMENT REGARDING FEDERALLY SPONSORED RESEARCH OR DEVELOPMENT

Not Applicable.

FIELD OF THE INVENTION

This invention relates to production and use of host cells for control of replication of plasmids, including, but not limited to, DNA vectors, in the host cells, and to their use for production of DNA, RNA and/or polypeptides encoded by DNA contained in these plasmids.

BACKGROUND OF THE INVENTION

Plasmids are normally circular, extrachromosomal DNA molecules that replicate autonomously within the cells of host organisms. The cells of many unicellular organisms, including some bacteria, contain naturally occurring wild-type plasmids that contribute various functions to the host cells such as antibiotic resistance and fertility. These wild-type plasmids and derivatives of them are the basic tools of recombinant DNA technology, providing vehicles for the transformation of the cells of host organisms with foreign DNA sequences which code for production, within the transformed cells, of corresponding foreign products. As used herein, "foreign products" means DNA, RNA and/or polypeptides that are foreign to the host cells including but not limited to DNA sequences encoding foreign genes, RNA molecules transcribed from inserted additional foreign DNA sequences, and polypeptides encoded by foreign genes.

Recombinant plasmids, similar to the parent plasmids from which they are derived, are capable of autonomous replication within host cells, and on replication, reproduce not only the DNA sequences of the parent plasmid but also the inserted additional DNA sequences, including the foreign genes. During polypeptide synthesis, transcription and translation of the DNA sequences of the recombinant plasmids carried within transformed host cells give rise to the synthesis of foreign RNA and polypeptides.

One factor which affects the yield of synthesized foreign product is the number of copies of the foreign gene which are present within the transformed cells, i.e. the copy number at which the recombinant plasmid is maintained within the host cells, this being defined normally as the number of copies of the plasmid per host genome. Generally speaking, the higher the copy number of the recombinant plasmid the greater is the yield of foreign product. Both low-copy-number plasmids, usually maintained within host cells at about 1-10 copies per genome, and high copy number plasmids, usually maintained at from 11 up to several hundred copies per genome, are known. The copy number of a given wild-type replicon is controlled by DNA sequences surrounding and including a DNA sequence that defines the origin of replication ("ori"). Thus, hereinafter we refer to high copy number and low copy number ori's.

High copy number plasmids have been used in recombinant systems with a view to obtaining good yields of foreign products. This can lead to undesirable results, however, since many such high copy number plasmids tend not to be maintained stably within transformed cells and may be lost from the cells before they can be grown to sufficient levels to permit bulk production of foreign products. For example, the foreign product may be toxic and/or inhibit propagation of the transformed cells, or the high copy number plasmids themselves may be inherently unstable or recombine with DNA sequences in other copies of the recombinant plasmid that are present in the same cell.

It is known that the copy numbers of some plasmids can be amplified above normal levels by inhibition of protein synthesis, such as, by addition of protein synthesis inhibitors such as chloramphenicol to the fermentation medium. However, protein synthesis is required for production of most gene products, and therefore the inhibitor must be removed before synthesis of foreign products can take place. The removal of inhibitor requires complicated manipulations and is not always possible.

Other solutions have also been proposed to overcome the problem of stable maintenance of high copy number plasmids in host cells. For example, in U.S. Pat. Nos. 4,487,835; 4,495,287; and 4,499,189, incorporated herein by reference, Uhlin et al. disclosed the use of mutant plasmids having a temperature-dependent plasmid copy number pattern such that the plasmid shows a controlled constant plasmid copy number when host bacteria carrying the plasmid are cultivated at one temperature and a much higher or totally uncontrolled copy number when the host bacteria carrying the plasmid are grown at a different temperature. Thus, cells may be propagated to desired production size culture at one temperature at which the plasmid replicates at low copy number and at which its gene products do not significantly inhibit cell growth. The temperature may then be altered, greatly increasing the plasmid copy number and also the corresponding production of gene products. However, temperature-dependent copy number may be limited to particular mutant plasmids, which may or may not contain suitable restriction enzyme cloning sites for a particular foreign DNA sequence. Also, introduction of copy number temperature dependence may introduce a source of instability into the plasmid, and these mutant plasmids may be unstable or subject to loss when cells carrying them are propagated over a prolonged period of time. Another disadvantage of this approach is the fact that higher temperatures may have a negative impact on protein stability.

In U.S. Pat. No. 5,015,573, Yarranton et al., incorporated herein by reference, disclosed a new class of vectors to solve the problem of stable low-copy maintenance of the vector while permitting replication at high copy number under a different set of conditions to produce a high yield of gene product. These vectors had two origins of replication. When propagated under a first set of conditions, replication takes place using the first on and results in a low copy number and stable inheritance of the vector or recombinant vector containing foreign DNA. Then, when propagated under a second set of conditions, replication takes place using a second, controllable ori, which is under the control of an inducible promoter. In one embodiment of this invention, the natural promoter which promotes transcription of the RNA species (RNAII or a similar species) that provides a primer for initiation of DNA replication by formation of a complex at or near the origin of replication is replaced by a controllable promoter. If a heterologous cloned gene is also under the control of a controllable promoter, both replication and expression of the gene are controllable from their respective promoters.

Like the invention disclosed by Yarranton, et al. U.S. Pat. No. 6,472,177 of Szybalski et al. and U.S. Pat. No. 5,874,259 of Szybalski, both incorporated herein by reference, disclosed compositions and methods for controlling copy number of a plasmid, including a BAC plasmid, wherein the plasmid contains two origins of replication. According to U.S. Pat. No. 6,472,177, which primarily discusses compositions and methods for dual control of both replication and transcription, "the conditional origin is provided in addition to a origin of replication that maintains the vector at a single copy per cell," and "the conditional on could be any on that functions in the host cell and is normally inactive until exposed to the replication-inducing agent." Thus, neither Yarranton nor Szybalski disclose compositions or methods for controlling plasmid copy number by controlling replication from a single ori.

U.S. Pat. No. 6,165,749 of Sagawa et al., incorporated herein by reference, also discloses vectors and methods for controlling the expression of a desired gene by a combination of two control mechanisms, i.e., by control of the copy number of the vector containing the gene and by control of transcription of the gene via an inducible promoter attached to an RNA polymerase gene. Use of these two control mechanisms enabled successful expression of a restriction enzyme that was toxic to the host cell when expressed without control of copy number of the vector containing the gene. In the case of this invention, the control of plasmid copy number was obtained by placing the RNAII gene, a replication pre-primer for initiation of replication from the plasmid ori, under an inducible promoter. Induction of the gene for RNAII resulted in an increase in copy number of plasmids containing the ori.

While the compositions and methods disclosed in the art provide solutions for controlling copy number of recombinant plasmids for particular applications, they suffer from certain disadvantages. All of the methods are limited to vectors having particular additional genetic elements, genes or other modifications. For example, the method of Uhlin et al. requires the use of a vector containing a particular mutation that causes temperature-sensitivity. The methods of Yarranton et al. and of Szybalski et al. require the use of vectors with two origins of replication, which increases the size of the vector and in most cases will limit the number and kind of restriction enzyme sites available for cloning of foreign genes. The method of Sagawa is limited to vectors that contain particular inducible RNAII-encoding DNA sequences for high-copy replication of the vector and, in most cases, an inducible RNA polymerase gene for transcription of a foreign gene that is cloned in the vector.

What is needed in the art are host cells and methods that enable copy-number control of replication of a broad range of widely-available plasmids from ori's that are capable of low-copy replication under one set of conditions and of high-copy replication under another set of conditions.

What is needed are host cells and methods that do not require modification or genetic engineering of the plasmid in order to control the copy number of the plasmid or of recombinant clones made using the plasmid.

Preferably, what is needed are host cells and methods for easily maintaining commonly-used plasmids and plasmid clones at low copy number for stable maintenance of clones and minimal loss of cloned DNA sequences that would be toxic or detrimental to the host cell at high copy number, and yet, which permit the plasmid and plasmid clones to be induced to high copy number in a tightly-controlled manner by means of simple reagents or conditions in order to obtain larger amounts and therefore, also, a higher purity of foreign products for the desired application.

Most preferably, what is needed are host cells and methods for inducible control of replication and copy number of a broad range of plasmids that have ori's with antisense-mediated replication control mechanisms, such as plasmids having ori's of the types contained in ColE1- and R1-type plasmids.

BRIEF SUMMARY OF THE INVENTION

In a preferred aspect, the present invention is a host cell for controllably changing the level of replication and copy number of a plasmid that is introduced into said host cell, wherein said host cell comprises a poly(A) polymerase gene that is operably joined to a conditionally inducible promoter, and wherein induction of said poly(A) polymerase gene results in a change in the copy number of said plasmid in said host cell by catalyzing polyadenylation of an antisense RNA molecule that affects initiation of replication from an origin of replication in said plasmid.

A primary object of the present invention is to provide host cells and methods for making and using host cells that enable control of copy number for a broad range of plasmids, including, but not limited to commonly used vectors, having an origin of replication that is regulated by an antisense RNA molecule, wherein polyadenylation of said antisense RNA molecule affects copy number of the plasmid in said host cell. Another primary object of the present invention is to provide host cells and methods for making and using said host cells that are capable of low-copy replication of plasmids having ori's of the present invention, such as, but not limited to, plasmids with ColE1-type ori's, under one set of conditions and of high-copy replication of these same plasmids from said on under another set of conditions.

Another object of the present invention is to improve cloning by permitting control of clone copy number at will. Another object of the invention is to improve sequencing, particularly high throughput sequencing, by permitting control of clone copy number at-will, most particularly by permitting control of clone copy number for clones in BAC, fosmid, and plasmid vectors.

Another primary object of the invention is to provide improved host cells and methods that permit successful cloning and stable maintenance at low plasmid copy number per cell of DNA comprising repetitive sequences, or AT-rich or GC-rich sequences, or sequences that are toxic or detrimental for the host cell, including without limitation, sequences that comprise one or more genes that encodes one or more peptides or proteins which is toxic or detrimental for the host cell when expressed. In short, another primary object of the invention is to provide host systems that permit successful cloning and stable maintenance of difficult-to-clone sequences at approximately one copy per cell, but which can be easily and rapidly induced to higher copy number on demand.

It is an object of the present invention to produce heterologous polypeptides in a host cell, even where the polypeptide is toxic or has other adverse effects on the host cell that would prevent cloning and/or stable maintenance of inserted polynucleotide prior to the overproduction of the polypeptide in conventional cell-based protein expression systems.

It is a further advantage of the present invention that the host cells are able to produce large quantities of a heterologous polypeptide, even toxic polypeptides, because the cells both amplify the plasmid and transcribe the DNA quickly after induction. Before induction, a leaky transcriptional promoter can have little effect on the cells, because the plasmid copy number is so low.

Notations and Nomenclature

The terms used herein have the following meaning with respect to the present invention:

As used herein, a "plasmid" is a DNA molecule that can replicate autonomously following its introduction into a host cell, including but not limited to, a DNA molecule in which other DNA, including, but not limited to, "foreign" or "heterologous" DNA can be operably joined. By way of example, but not of limitation, a plasmid of the invention can be a vector, BAC, fosmid, a P1 vector, episome, or any other suitable DNA molecule.

The words "foreign" or "heterologous" refer to the fact that the DNA which is operably joined to the plasmid is not normally present in the host cell in which it is replicated. The most common method by which the DNA is "operably joined" to a plasmid is by covalent joining of compatible ends by means of an enzyme referred to as a ligase, such as, but not limited to, T4 DNA ligase, by a process referred to as "ligation." However, the invention also includes any other method for joining or "ligating" foreign DNA into a plasmid including, but not limited to, chemical joining or joining by methods known in the art that use a topoisomerase. The process of ligating a DNA molecule in a plasmid and then replicating this molecule in a host is referred to as "cloning" or "molecular cloning".

As used herein, an "inducing agent" is a substance that activates the promoter, either by positively regulating the transcription from the promoter, or by binding to a repressor that would otherwise inhibit transcription from the promoter. In either case, the inducer activates transcription from an inducible promoter.

In this application, "operably joined" means that the promoter is situated upstream of the polynucleotide coding sequence such that productive transcription of the polynucleotide is initiated at the promoter. The term "polypeptide" broadly encompasses all proteinaceous molecules including, without limitation, oligopeptides, peptides and proteins, as those terms are understood in the art.

BRIEF DESCRIPTION OF THE FIGURE

The following FIGURE forms part of the present specification and is included to further demonstrate certain aspects of the present invention. The invention may be better understood by reference to this FIGURE in combination with the detailed description of specific embodiments presented herein.

Figure 1:
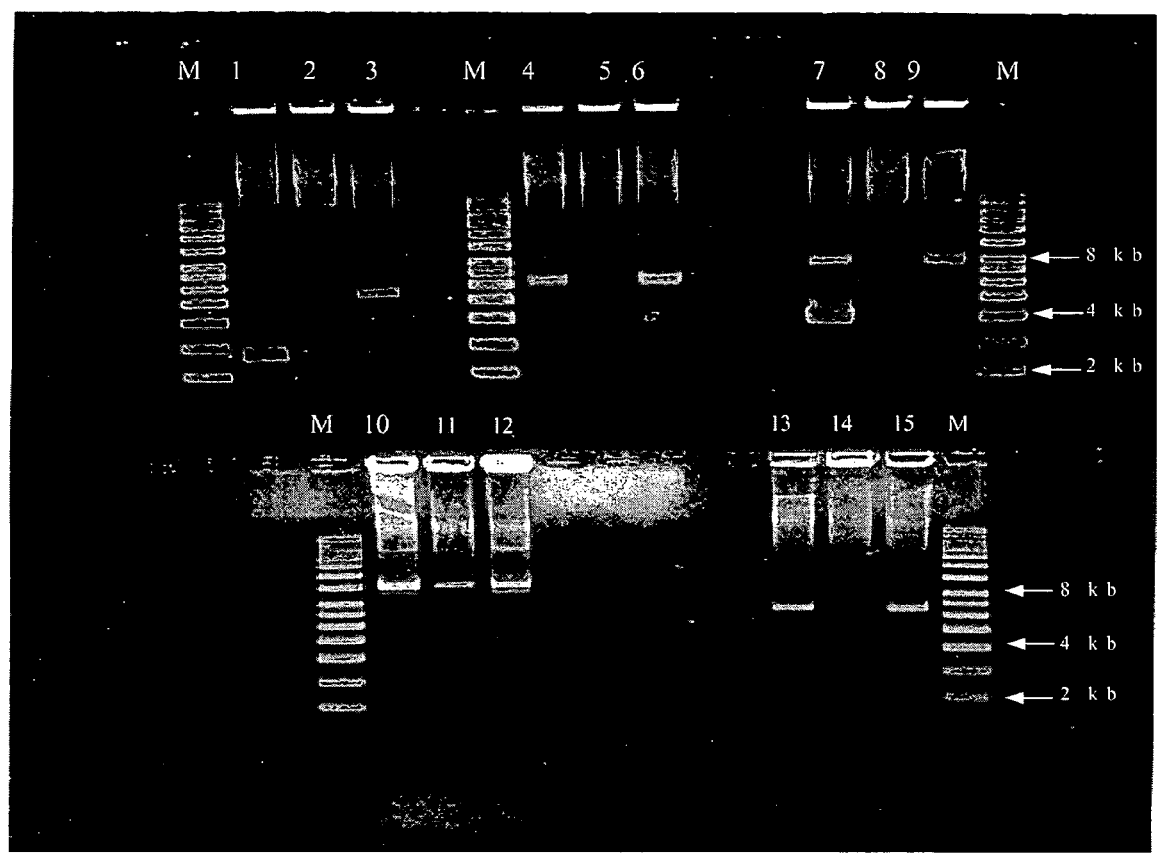
FIG. 1 shows plasmid preparations obtained from control clones that did not comprise a pncB gene operably joined to a conditionally inducible promoter ("control"), plasmid preparations from clones that comprised a pcnB gene operably joined to a conditionally inducible promoter, which clones had been grown under conditions that induced an increase of plasmid copy number through the addition of an inducing agent ("induced"), and plasmid preparations from clones that comprised a pcnB gene operably joined to a conditionally inducible promoter, which clones had been grown under conditions that did not induce an increase of plasmid copy number, because no inducing agent was added ("uninduced").

The lanes marked with an "M" show a supercoiled molecular weight marker, the arrowheads indicate bands of DNA of 2 kb, 4 kb, and 8 kb. Lane 1 shows the plasmid preparation of TransforMax™ EC100™-T1$^R$ cells containing pUC19 plasmids (control); lane 2 shows the plasmid preparation of pcnB-<araBpcnB> Clone#4 cells containing pUC19 plasmids grown without the addition of an inducing agent (uninduced); lane 3 shows the plasmid preparation of pcnB-<araBpcnB> Clone#4 cells containing pUC19 plasmids grown with the addition of arabinose as an inducing agent (induced); lane 4 shows the plasmid preparation of TransforMax™ EC100™-T1$^R$ cells containing pET11a/rnhA plasmids (control); lane 5 shows the plasmid preparation of pcnB-<araBpcnB> Clone#4 cells containing pET11a/rnh plasmids grown without the addition of an inducing agent (uninduced); lane 6 shows the plasmid preparation of pcnB-<araBpcnB> Clone#4 cells containing pET11a/rnh plasmids grown with the addition of arabinose as an inducing agent (induced); lane 7 shows the plasmid preparation of TransforMax™ EC100™-T1$^R$ cells containing TOPO® TA plasmids (control); lane 8 shows the plasmid preparation of pcnB-<araBpcnB> Clone#4 cells containing TOPO® TA plasmids grown without the addition of an inducing agent (uninduced); lane 9 shows the plasmid preparation of pcnB-<araBpcnB> Clone#4 cells containing TOPO® TA plasmids grown with the addition of arabinose as an inducing agent (induced); lane 10 shows the plasmid preparation of TransforMax™ EC100™-T1$^R$ cells containing pMOD<pCC-BAC> plasmids (control); lane 11 shows the plasmid preparation of pcnB-<araBpcnB> Clone#4 cells containing pMOD<pCC-BAC> plasmids grown without the addition of an inducing agent (uninduced); lane 12 shows the plasmid preparation of pcnB-<araBpcnB> Clone#4 cells containing pMOD<pCC-BAC> plasmids grown with the addition of arabinose as an inducing agent (induced); lane 13 shows the plasmid preparation of TransforMax™ EC100™-R1$^R$ cells containing pHC79 plasmids, which are also referred to as "fosmids" (control); lane 14 shows the plasmid preparation of pcnB-<araBpcnB> Clone#4 cells containing pHC79 fosmids grown without the addition of an inducing agent (uninduced); and lane 15 shows the plasmid preparation of pcnB-<araBpcnB> Clone#4 cells containing pHC79 fosmids grown with the addition of arabinose as an inducing agent (induced).

DETAILED DESCRIPTION OF THE INVENTION

Two types of mechanisms basically control the replication of plasmid DNA. One utilizes a series of repeated sequences, designated iterons, which are capable of interacting with a protein that initiates DNA replication. In the other type of mechanism, antisense RNA molecules hybridize with the RNA molecule that is responsible for the initiation of plasmid replication. The replication of plasmids and mechanisms of control of replication of plasmids are reviewed by L. Actis et al. (Frontiers in Bioscience, 3: d43-62, 1998), by S. Brantl (Plasmid, 48: 165-173, 2002), by G. del Solar and M. Espinosa (Molecular Microbiol., 37: 492-500, 2000), by G. del Solar et al. (Microbiology and Molecular Biology Reviews, 62: 434-464, 1998), and earlier, by Y. Eguchi et al. (Annu. Rev. Biochem., 60: 631-652, 1991) and by K. J. Marians (Annu. Rev. Biochem., 61: 673-719, 1992), all of which are incorporated herein by reference.

The replication of ColE1 and related plasmids is well characterized. ColE1-type plasmids, of which ColE1 plasmid itself is an example, have plasmid replication systems having a number of features in common. These features include a DNA sequence defining an origin of replication and upstream thereof a DNA sequence coding for transcription, in opposing directions, of two RNA species, RNAII and RNAI. The RNAII species provides an RNA primer, sometimes called a "pre-primer", that anneals at or near the origin from which DNA synthesis is initiated (forming an initiation complex), and is then processed by RNase H to generate the 3'-end of the replication primer. DNA polymerase I and other host proteins then replicate the plasmid DNA by extending the RNase H generated end of the RNAII primer. ColE1 plasmids and plasmids having a similar mechanism for initiation of replication are defined as "ColE1-type" plasmids herein.

The RNAI species, which is complementary to a portion of the RNAII species (i.e., is an antisense molecule to RNAII) interferes with the formation of this initiation complex. Transcription of the two RNA species are controlled by separate promoter sequences associated with the DNA sequences which code for their transcription. Plasmids containing a ColE1-type origin of replication are widely used for cloning, for in vitro transcription, and for gene expression purposes in *Escherichia coli* and in some other prokaryotes.

A second type of mechanism in which antisense RNA molecules hybridize with mRNA molecules involved in the initiation of plasmid replication is found in the R1 plasmid. Replication of R1 is initiated by a protein, known as RepA protein, and the RepA mRNA, called CopT (for "Cop target"), is regulated by an antisense RNA called CopA. CopA controls initiation of R1 replication by interacting with CopT, causing posttranscriptional inhibition of RepA synthesis. R1 and plasmids having a similar mechanism for initiation of replication are defined as "R1-type" plasmids herein. The R1-type of plasmid replication was characterized by P. Blomberg et al. (Mol. Microbiol., 12: 49-60, 1994), P. Blomberg et al. (Embo J., 11: 2675-2683, 1992), P. Blomberg et al. (Embo J., 9: 2331-2340, 1990), C. Malmgren et al. (J. Biol. Chem., 272: 12508-12512, 1997), K. Nordstrom et al. (Gene, 72: 237-240, 1988), P. Stougaard et al. (Proc. Natl. Acad. Sci. USA, 78: 6008-6012, 1981), E. Wagner et al. (Embo J., 11: 1195-1203, 1992), and C. Malmgren et al. (RNA, 2: 1022-1032, 1996), all of which are incorporated herein by reference.

In addition to the RNAII primer, the RNAI antisense molecule, the CopT mRNA, and the CopA antisense RNA, other molecules are also known that affect copy number of plasmids with antisense RNA regulated origins of replication. By way of example, but not of limitation, a protein encoded by the pcnB gene is known to have an effect on copy number of ColE1-type plasmids and R1-type plasmids in *E. coli* (L. Actis et al., Frontiers in Bioscience, 3: d43-62, incorporated herein by reference, and F. Soderbom and E. Wagner, Microbiology 144: 1907-1917, 1998, incorporated herein by reference).

The pcnB gene was first identified by J. Lopilato et al. (Mol. Gen. Genet., 205: 285-290, 1986) based on an *E. coli* chromosomal mutation that substantially reduced the copy number of ColE1-type plasmids, which led them to designate the locus causing this as pcnB for "plasmid copy number". The *E. coli* gene was subsequently cloned and sequenced (J. March et al., Mol. Microbiol., 3: 903-910, 1989; and J. Liu and J. Parkinson, J. Bacteriology, 171: 1254-1261, 1989) and later, evidence was provided that the pcnB locus encodes a poly(A) polymerase protein (G. Cao and N. Sarkar, Proc. Natl. Acad. Sci. USA, 89: 10380-10384, 1992). Without being bound by theory, it is believed that that the rapid degradation of RNAI is associated with polyadenylation of the RNA and that this process is mediated by poly(A) polymerase (L. He et al., Mol. Microbiol., 9: 1131-1142, 1993; and F. Xu et al., Proc. Natl. Acad. Sci. USA, 90: 6756-6760, 1993).

The absence of poly(A) polymerase intermediates causes the intracellular accumulation of RNAI decay products that have antisense activity and can inhibit initiation of plasmid replication, resulting in a reduced copy number of ColE1-type plasmids (L. He et al., Mol. Microbiol., 9: 1131-1142, 1993; and F. Xu et al., Proc. Natl. Acad. Sci. USA, 90: 6756-6760, 1993). In addition to mediating the degradation of RNAI, polyadenylation is also believed to decrease the interaction of RNAI with its RNAII target thus affecting the copy number of ColE1-type plasmids (F. Xu et al., Plasmid, 48: 49-58, 2002). M. Masters et al. (J. Bacteriol., 175: 4405-4413, 1993) found that strains deleted for pcnB grow normally demonstrating that the pcnB gene is dispensable in *E. coli*. All publications cited within this paragraph are incorporated herein by reference.

The role of the pcnB gene was further studied by U. Binnie et al. (Microbiol., 145: 3089-3100, 1999); F. Xu and S. Cohen (Nature, 374: 180-183, 1995); C. Ingle and S. Kushner (Proc. Natl. Acad. Sci. USA, 93: 12926-12931, 1996); J. Jasiecki and G. Wegrzyn (EMBO Rep., 4: 172-177, 2003); N. Binns and M. Masters (Mol. Microbiol., 44: 1287-1298, 2002); S. Yehudai-Resheff and G. Schuster (Nucleic Acids Res., 28: 1139-1144, 2000); L. Raynal and A. Carpousis (Mol. Microbiol., 32: 765-775, 1999); E. Hajnsdorf and P. Regnier (J. Mol. Biol., 286: 1033-1043, 1999); Z. Li et al. (Proc. Natl. Acad. Sci. USA, 95: 12158-12162, 1998); F. Soderbom et al. (Mol. Microbiol., 26: 493-504, 1997); N. Sarkar (Microbiology, 142: 3125-3133, 1996); L. Raynal et al. (Biochimie, 78: 390-398, 1996); G. Cao et al. (Proc. Natl. Acad. Sci. USA, 93: 11580-11585, 1996); and M. Masters et al. (Mol. Gen. Genet., 220: 341-344, 1990).

The host cell strain of the present invention is preferably bacterial, preferably an *E. coli* strain, but the host cell can be any cell in which a plasmid replicates using an ori from which the level of replication is controllable by induction of a poly (A) polymerase gene that is operably joined to a conditionally inducible promoter. The host cell can be a plant, yeast or other fungal cell, or even an animal cell, including a mammalian cell, as long as the ori is selected so as to function in the selected host. One could also employ shuttle vectors incorporating a suitable ori that functions in the host cell that is used according to the present invention. C. Hamilton (Gene, 200: 107-116, 1997), incorporated herein by reference, describes a binary-BAC shuttle vector for use also in plant cells, but without the presently disclosed plasmid copy number control feature. A host cell can also be a cell that is genetically engineered to support replication of a plasmid the copy number of which is mediated by a poly(A) polymerase that polyadenylates an antisense RNA that controls replication.

A plasmid used with a host cell of the present invention can be any plasmid that has an ori wherein initiation of replication from said ori is controlled, at least in part, by an antisense RNA and wherein polyadenylation of said antisense RNA results in a change in the level of replication and of the copy number of said plasmid.

In some embodiments, the ori can be an ori wherein replication is initiated from an RNA pre-primer with which the antisense RNA interacts. By way of example, but not of limitation, plasmids having this type of ori comprise ColE1-type plasmids, including, but not limited to the following, for which the corresponding references are incorporated herein: ColE1 and pMB1 (F. Bolivar, Life Sci., 25: 807-817, 1979; A. Bhagwat and S. Person, Mol. Gen. Genet., 182: 505-507, 1981), p15A, pJHCMW1 (K. Dery et al., Plasmid, 38: 95-105, 1997; this is a *Klebsiella pneumoniae* plasmid), pSW100 (J. Fu et al., Plasmid, 34: 75-84, 1995; this is an *Erwinia stewartii* plasmid), pEC3 (N. Nomura and Y. Murooka, J. Ferment. Bioeng., 78: 250-254, 1994; this plasmid is from *Erwinia carotovora* subsp. *carotovora*), pBR322 and other plasmids of the pBR series (P. Balbas et al., Biotechnol., 10: 5-41, 1988; L. Covarrubias et al., Gene, 13: 25-35, 1981), of the pUC series of plasmids (J. Viera and J. Messing, Gene, 19: 259-268, 1982), the pET series (F. Studier, et al., Methods Enzymol., 185: 60-89, 1990), the pBluescript™ series, the pBAD series, a plurality of vectors of the Gateway™ series, a plurality of vectors of the TOPO® series, pAT153, NTP1, CloDF13, RSF1030, P15A, and many other vectors that have an ori that is regulated by an antisense RNA molecule, wherein polyadenylation of the antisense RNA molecule has an effect on the copy number of the plasmid.

The invention is not limited to host cells that are only for inducible modification of copy number of plasmids with ColE1-type origins of replication. Still other plasmids that can be used with host cells of the present invention can comprise an ori wherein replication is initiated by means of a protein that is encoded by an mRNA with which the antisense RNA interacts. Thus the invention also comprises host cells and methods to make and use host cells for plasmids having other origins of replication wherein replication from the ori is regulated by an antisense RNA molecule and wherein polyadenylation of an antisense RNA molecule results in a change in the copy number of the plasmid. By way of example, but not of limitation, it is also known in the art that R1-type plasmids regulate initiation of replication via an antisense RNA molecule (E. Wagner and R. Simons, Annu. Rev. Microbiol., 48: 713-742, 1994, incorporated herein by reference).

By way of example, but not of limitation, R1-type plasmids comprise the following plasmids: IncFII plasmids, which include R1, R100, and R6, R6-5, RP4, other related genetic elements belonging to the IncFIIa, IncFIFc, IncFIII, and IncFVII groups, as well as pUB100 and pC194 which exemplify Staphylococcal plasmids.

The invention comprises any host strain that permits inducible control of plasmid copy number for any plasmid wherein replication of the plasmid is controlled in some manner by an antisense RNA molecule and wherein inducible control of a poly(A) polymerase in said host cell affects the copy number of said plasmid in said host cell. Thus, host cells and methods for controlling copy number of R1-type plasmids are within the scope of the present invention.

In preferred embodiments of the invention, if the cell that is used to make a host cell of the invention has a constitutively-expressed poly(A) polymerase gene that catalyzes polyadenylation of an antisense RNA molecule that is involved in control of replication from the ori, this constitutively-expressed gene is either removed by homologous recombination or other methods known in the art or is inactivated using a method such as, but not limited to, transposon insertion, or other random or site-specific mutagenesis techniques that are well known in the art, and is replaced by a poly(A) polymerase gene that is operably joined to an inducible promoter. Preferably, the level of endogenous expression in the host cell of the poly(A) polymerase that polyadenylates the antisense RNA is zero or undetectable.

However, in some embodiments, if the level of an endogenous poly(A) polymerase gene is very low, it may not be essential according to the present invention to remove or inactivate an endogenous poly(A) polymerase gene of the host cell. The level of endogenous poly(A) polymerase activity that is acceptable in a particular host cell of the invention can vary with the effect of poly(A) polymerase activity on copy number of a particular plasmid, which in turn can vary based on other factors, such as the particular ori used, and the relative level of the antisense RNA that is involved with regulation of replication. It will also be understood by those with knowledge in the art that mutant forms of the poly(A) polymerase can have different activities in polyadenylation of the antisense RNA and that the acceptable endogenous level of expression of the poly(A) polymerase protein in a host cell of the invention can vary accordingly.

In an important embodiment of the invention, the controllable replication systems may be prepared by replacement of the natural promoter that promotes transcription of a poly(A) polymerase gene by a controllable promoter. Alternatively, the natural promoter may be used and transcription of the poly(A) polymerase made controllable by incorporating a regulating function, such as, but not limited to, an operator sequence, e.g. the lac operator or $O_L$ or $O_R$ operators of phage lambda, into the transcription system.

The poly(A) polymerase gene that is operably joined to a conditionally inducible promoter in a host cell of the invention can be any gene that encodes a protein that polyadenylates an antisense RNA that affects plasmid copy number. A preferred poly(A) polymerase gene of the invention for *E. coli* host cells is a pcnB gene that encodes a poly(A) polymerase I protein. Similar genes that encode poly(A) polymerase genes are also known for other cells, some of which a skilled artisan can easily find by conducting a sequence similarity search of U.S. or international sequence databases, such as, but not limited to, a BLAST® (Basic Local Alignment Search Tool) search.

The invention comprises any and all host cells that use any poly(A) polymerase that polyadenylates an antisense RNA that changes the level of replication and copy number of a plasmid that is introduced into that host cell.

The invention also comprises mutant forms of poly(A) polymerase genes and their corresponding proteins that are active for the purposes of the invention, and such mutant genes, and their encoded proteins can be desirable in some embodiments in order to modify (either increase or decrease) copy number of particular plasmids or plasmid clones for a particular purpose. In one aspect of these embodiments said mutant forms of poly(A) polymerase genes have a higher rate of translation than the wildtype poly(A) polymerase gene. In some embodiments of the invention a plurality of poly(A) polymerase genes is inserted into the host cell chromosome which increases the level of expression of poly(A) polymerase.

In most embodiments of host cells of the invention, which are preferred embodiments, the poly(A) polymerase gene that is operably joined to a conditionally inducible promoter is inserted in the chromosome of the a host cell. However, the invention also envisions embodiments in which the poly(A) polymerase gene that is operably joined to a conditionally inducible promoter is in another extrachromosomal genetic element, such as in a mitochondrial DNA or in another plasmid that is compatible in the host cell with the plasmid the copy number of which is changed by said conditionally expressed poly(A) polymerase. Preferably, if the conditionally expressible poly(A) polymerase gene is in a plasmid or other extrachromosomal element, the plasmid containing the gene is at low copy number in the host cell, since it has been shown that induction of expression of a pcnB-encoded poly (A) polymerase from a multicopy plasmid in an *E. coli* cell can be toxic to the cell (B. Mohanty and S. Kushner, Mol. Microbiol., 34: 1094-1098, 1999, incorporated herein by reference).

Inducible promoters are known to the art and a detailed summary of the state of the art is not provided herein. A suitable inducible promoter functions in the selected host cell and responds to an inducing agent with sufficient strength to promote a high level of transcription of a downstream polynucleotide operably joined to the inducible transcriptional promoter in the plasmid.

Before induction the promoter should normally be inactive, resulting in insignificant or undetectable levels of product as measured by conventional detection methods in the non-induced state. It is also preferred that the promoter require only a single agent for induction. Although the inducible promoter could be any promoter having these attributes, preferred inducible promoters are the araC-$P_{araBAD}$ (activator gene)-promoter (araC-$P_{araBAD}$; GenBank Accession No. X 81838 nt 1-1277) and the TetR/$P_{LtetO}$ repressor promoter ($P_{LtetO}$; GenBank Accession No. U 66312). These promoters are preferable because they are tightly regulated when non-induced, and very strong when induced. These two promoters can be activated by treating the host cells with 0.01% L-arabinose (LA) and 100 ng/ml anhydrotetracycline (aTc), (R. Lutz and H. Bujard, Nucleic Acids Res., 25: 1203-1210, 1997, incorporated herein by reference), respectively. Concentrations of LA and aTc shown above are believed optimal but are not essential. AraC/$P_{araBAD}$ also responds to an anti-inducer, D-fucose. Thus, the activity of AraC/$P_{araBAD}$ can be regulated by adjusting the LAND-fucose ratio. Other suitable promoters include, but are not limited to, $P_{tac}$, and a phage promoter under inducible control such as but not limited to a T3 promoter, a T5 promoter, a T7 promoter, and an SP6 promoter.

The origin of replication, the RNA coding sequences and associated promoters together, and other genes that encode proteins that affect the level, stability, or interaction of antisense RNA molecules with a replication primer or mRNA provide an internally self-regulated system which controls the replication incompatibility and the copy number of plasmids having a replication system that is controlled by antisense RNA. The present invention comprises host cells and methods for making and using these host cells for controlling copy number of plasmids having a ColE1-type origin of replication or an R1-type origin of replication.

The present invention is not intended to comprise compositions or methods for controlling copy number plasmids in which control of replication from the respective ori does not involve an antisense RNA molecule. By way of example, compositions or methods for controlling copy number of plasmids using the oriV origin of replication are excluded from the scope of the present invention.

Another embodiment of the invention is a host cell that comprises a poly(A) polymerase gene operably joined to a conditionally inducible promoter, wherein said host cell also comprises another gene, such as, but not limited to a gene encoding an RNA polymerase, that is operably joined to a conditionally inducible promoter. In a first aspect of this embodiment, the conditionally inducible promoter that is operably joined to another gene, such as, but not limited to, a gene encoding an RNA polymerase, is different from the conditionally inducible promoter to which the poly(A) polymerase is operationally joined. In a second aspect of this embodiment, the conditionally inducible promoter that is operably joined to another gene, such as but not limited to, a gene encoding an RNA polymerase, is the same as the conditionally inducible promoter to which the poly(A) polymerase is operationally joined.

The inducible promoters used for the present invention can be activated by suitable signals in a host cell of the invention. The inducing agents can be positive regulators or can interact with negative regulators to increase amplification and transcription as desired. A positive regulator (inducer) acts by providing a signal that increases an activity while a negative regulator (repressor) prevents an activity until an agent (also historically designated as inducer) prevents the negative regulation.

The agents can be organic or inorganic chemical agents or can be polypeptides encoded by polynucleotide sequences in the host cell genome or on an extrachromosomal plasmid present in the host cell. Alternatively, the agents can be administered manually to the host cells by, e.g., providing the agent in the growth medium.

The skilled artisan will appreciate that it is within the level of skill in the art to provide as simple or as complex a regulatory scheme as desired for ensuring that the appropriate inducing agent is available for inducing activity of the poly (A) polymerase or other gene at the appropriate time. The precise nature of that scheme is not critical to the invention. Rather, for purposes of this invention, it is understood that the ultimate agents for amplifying the plasmid and for inducing transcription can be provided as needed.

Plasmids can be inserted into the host cells of the invention using standard nucleic acid transfer methods, such as, but not limited to, electroporation, calcium-mediated transformation or cos-mediated phage lambda packaging and transfection.

By means of processes of the invention, transformed host cells are propagated to give the cultures required for economic production of DNA, RNA, polypeptides or other products under conditions where the plasmid replicates at low copy number and the instability problems associated with high copy number plasmids are avoided, followed by induction of replication wherein the plasmid replicates at high copy number with concomitant high yield of polynucleotide, polypeptide, protein or other products.

In addition to poly(A) polymerase genes that polyadenylate antisense RNA molecules that bind to an RNA pre-primer or to an mRNA that encodes an initiator protein, the invention also envisions that other genes that are involved in the maturation of an initiator protein or a primer required for initiation of replication can be used to make host cells and methods for conditional control of plasmid copy number. By way of example, but not of limitation, a small nonessential polypeptide called the Rop or Rom protein appears to increase the efficiency of interaction and stability of interaction between the RNAI antisense molecule and the RNAII replication primer.

Also way of example, but not of limitation, host cells may be made which have conditional expression of genes that mediate the maturation of the RNAII primer of ColE1-type plasmids, such as, but not limited to, a gene that encodes a Rop or Rom Protein, a gene that encodes RNase E, a gene that encodes RNase H, or a gene that encodes RNAI.

Conditional expression of other genes that accelerate or restrain the formation of an initiator protein or primer may be used in addition to or in place of conditional expression of a poly(A) polymerase gene in order to make host cells and methods for modulation or fine tuning of plasmid copy numbers for particular applications. If host cells are made that permit conditional expression of more than one gene, the expression of those genes can be from the same inducible promoter or from different promoters that are induced independently by different inducers. Applications for using the host cell of the invention for modulation or fine tuning of plasmid copy numbers include but are not limited to fermentation processes involving the use of genetically engineered bacteria for the production of plasmid DNA, RNA, and recombinant polypeptides of interest.

It can further be envisioned that the present invention can be used in combination with a method for operably joining an RNAII gene or an RNAI gene to a conditionally inducible promoter for further fine-tuning of plasmid number control wherein said RNAII gene or said RNAI gene and said conditionally inducible promoter can be located on the host chromosome or another extrachromosomal genetic element, such as in another plasmid that is compatible in the host cell with the plasmid the copy number of which is changed by a conditionally expressed poly(A) polymerase.

EXAMPLES

Example I

Construction of Bacterial Strains

New *E. coli* host strains comprising at least one poly(A) polymerase gene operably joined to a conditionally inducible promoter were constructed using *E. coli* strain TransforMax™ EC100™-T1$^R$ (F-mcrA Δ[mrr-hsdRMS-mcrBC] 80dlacZΔM15 ΔlacX74 recA1 endA1 araD139 Δ(ara, leu) 7697 galU galK λ-rpsL nupG), which is commercially available from EPICENTRE.

*E. coli* strain TransforMax™ EC100™-T1$^R$, which contains a wild-type pcnB gene, was mutated by a targeted knockout of said gene which ceases its wild type function by a homologous recombination technique facilitated by the use of plasmid pKD46 which contains an IPTG inducible promoter operably linked to genes encoding phage A red, exo and bet proteins; said plasmid is available from the *E. coli* Genetic Stock Center (CGSC) at Yale University, CGSC No. 7739. The DHFR gene from the EZ::TN™ <DHRF-1> Transposon (available from EPICENTRE) was amplified by PCR using the FailSafe™ PCR System to have 45 bases homologous to the pcnB gene at the 5' and 3' ends of the DHFR gene, henceforth called the pcnB-DHFR cassette, by use of the primers with the following sequences:

Forward:
5'-CTCCAGCAGTTTCCATGCGCGTTTAC-CCTGACGACGGGACATAC GCGGATAGACGGCATG-CACGATTTG-3' [Sequence I.D. No. 1]; and Reverse:
5'TCCGTAACTGCCCGCCTGGTGGGTCGC-CGTTTCCGTCTGGCTCAT GGCAGGTCGACTCTA-GAGGATCCCCG-3' [Sequence I.D. No. 2].

This pcnB-DHFR cassette was then processed by PEG precipitation, phenol/chloroform extraction and ethanol precipitation, and re-suspended in 10 mm Tris; 1 mm EDTA ($T_{10}E_1$). Of the re-suspended DNA 200 ng were electroporated by standard techniques into the TransforMax™ EC100™-T1$^R$ cell line containing the pKD46 plasmid. Homologous recombinants of the wild type pcnB gene replaced with the pcnB-DHFR cassette were selected for on LB pates or Mueller-Hinton plates supplemented with 10 ug/ul trimethoprim. Recombinant clones were screened by the phenotype of maintaining a pUC19 vector, a pBAD vector, a pET vector, a pCC vector, and a pHC vector at a low copy number. Recombinants were also analyzed by PCR using the FailSafe™ PCR system with primers specific for the DHFR gene, and by the ability to grow on trimethoprim after sequential generations to ensure the stability of pcnB-DHFR cassette. Once an TransforMax™ EC100™-T1$^R$ pcnB mutant clone that had a reduced plasmid copy number, was able to grow on trimethoprim after sequential generations, and contained a DHFR gene was selected, the pKD46 plasmid was removed by growing the mutant at the pKD46 non-permissive temperature of 37° C. for sequential generations. The removal of the pdK46 plasmid was determined by the clones' inability to grow on ampicillin.

Then, the wild type pcnB gene was PCR amplified using the FailSafe™ PCR system from *E. coli* wild type strain MG1655 (available from the American Type Culture Collection (ATTC), ATTC No. 47076) genomic DNA using primers with the following sequences:

Forward: 5'-GCTATGATTAGCCGGAATTCTTTTGTC-CTG-3' [Sequence I.D. No. 3]; and

Reverse: 5'-CTGCCTATGGCAAGCTTCGCCACTGT-CATG-3' [Sequence I.D. No. 4].

This pcnB PCR product, henceforth referred to as the pcnB cassette, was digested with EcoRI and HindIII restriction enzymes and ligated into an EcoRI and HindIII digested sequence containing the araB promoter on a DNA fragment that contained an arabinose inducible operon, all with standard molecular techniques, and clones selected for on ampicillin. Clones were screened initially by size; clones with the correct size insert were grown up overnight, plasmid DNAs were mini-prepped and restriction mapped to verify the correct insert. Once a clone was selected to have the proper pcnB insert in the araB promoter containing DNA fragment, henceforth referred to as araB/pcnB, its mini-prep DNA was then digested with HindIII restriction enzyme and made blunt-ended using the End-It™ DNA End Repair Kit (EPICENTRE) according to the manufacturers protocol, and treated with shrimp alkaline phosphate to remove its free phosphate groups to prevent excess self-ligation.

Then a blunt ended DNA molecule with phosphorylated 5' ends comprising the kanamycin resistance gene from the EZ::TN™ <KAN-2> Transposon which is commercially available from EPICNTRE flanked by FLP recombination target (frt) sites on its 5' and 3' ends, henceforth referred to as the frt-kan cassette, was ligated into the HindIII, blunt, shrimp alkaline phosphate treated araB/pcnB construct and clones were selected for by the ability to grow on LB agar supplemented with ampicillin+kanamycin. Clones were then grown overnight in LB broth supplemented with ampicillin+kanamycin and mini-prepped to obtain DNA from each clone. In two different experiments clones were then restriction digested with two different restriction endonucleases, BamHI and ClaI, to map the orientation of the frt-kan-frt cassette relative to the araB/pcnB construct. Once a clone was found in the 5'-3' orientation relative to the pcnB gene, the whole arabinose inducible operon comprising the araC, araB promoter, pcnB gene, frt-kan cassette, and the rrnBT$_1$T$_2$ transcriptional terminator, henceforth referred to as the araBpcnB cassette, was PCR amplified using the FailSafe™ PCR system with primers having the following sequences:

Forward: 5'-CGTCAATTGTCTGATTCGTTACC-3' [Sequence I.D. No. 5] and Reverse: 5'-GAAGCATTTAT-CAGGGTTATTGTC-3' [Sequence I.D. No. 6].

This araBpcnB cassette PCR product was blunted and kinased then ligated into an EcoRI, blunt ended, shrimp alkaline phosphate treated pMOD-2™ plasmid (EPICENTRE) and selected for growth on LB agar supplemented with ampicillin+kanamycin. Clones were then grown overnight in LB broth supplemented with ampicillin+kanamycin and mini-prepped to obtain DNA from each clone. Clones were then restriction digested to map the orientation of the araBpcnB cassette relative to the pMOD-2™ plasmid and the correct clone with the araBpcnB cassette in 3'-5' orientation with respect to the pMOD-2™ plasmid was selected. An artificial Tn-5 based transposon containing the araBpcnB cassette was made by PCR using the FailSafe™ PCR system and multiple cloning site (MCS) PCR primers, which are commercially available form EPICENTRE, comprising the following sequences:

Forward: 5'-ATTCAGGCTGCGCAACTGT-3' [Sequence I.D. No. 7] and Reverse: 5'-GTCAGTGAGCGAG-GAAGCGGAAG-3' [Sequence I.D. No. 8].

The artificial Tn5 based transposon was then prepared by PvuII digestion using a protocol similar to one of the methods described for preparing EZ::TN™ Transposons in Product Literature No. 145 for the EZ::TN™ pMOD-2™ <MCS> Transposon Construction Vector (EPICENTRE). The resulting transposon is used to prepare Transposome™ complexes as described in the same Product Literature No. 145. Thousands of random insertion clones were obtained following electroporation of the transposome into the mutant Transfor-Max™ EC100™-T1$^R$ pcnB$^-$ cell line, the creation was described earlier in this example, and transposition clones were selected for on LB supplemented with trimethoprim+ kanamycin. Random clones were then chosen and analyzed for their ability induce to higher copy number upon addition of arabinose, which then allows for transcription of the pcnB gene from the araB promoter.

Cultures were started with the TransforMax™ EC100™-T1R cell line as a control and with the pcnB-<BADpcnB>clone#4 cell line, a cell line containing the araB-pcnB cassette. Each cell line contained one type of plasmid from the following group of plasmids: pUC19, pET11a/rnhA (a PET11 plasmid with a polypeptide encoding DNA insert named "rnhA"), TOPO® TA vector, pMOD-2™<pCC-BAC> (a pMOD-2™ vector containing the pCC1BACT™ vector as a DNA insert) and a pHC79 cosmid. After overnight growth 2 ml of the each culture was diluted to 50 ml with fresh LB and grown for 30 minutes. A sample from the cultures was taken for an uninduced sample. Then 200 µl of 10% arabinose was added to the rest of the cultures and the cultures were induced for 4 hours shaking at 37° C.

Plasmids were visualized from all cultures (control, uninduced, induced) for equal numbers of cells using a standard whole cell lysis protocol. Aliquots were run on agarose gels.

As shown in FIG. 1 the results indicated that the copy number of several plasmids including pUC19, pET11a, TOPO® TA, pMOD-2™ and pHC79 were increased through arabinose induction.

The invention claimed is:

1. A method for cloning and stably maintaining a DNA sequence encoding a foreign product in a host cell, said method comprising:

A. providing:
      (1) a host cell for conditional control of copy number of a recombinant plasmid that is introduced into said host cell, wherein said host cell comprises a poly(A) polymerase gene that (a) is operably joined to a conditionally inducible promoter, (b) is located on a chromosome of said host cell, and (c) catalyzes polyadenylation of an antisense RNA molecule that affects initiation of replication from an origin of replication (ori) in said recombinant plasmid wherein the copy number of the recombinant plasmid in the host cell is lower when the poly(A) polymerase gene is uninduced than when the poly(A) polymerase gene is induced, wherein said host cell additionally comprises an RNA polymerase gene operably joined to a conditionally-inducible promoter that is different from the conditionally-inducible promoter to which the poly(A) polymerase gene is operably joined; and
      (2) a DNA sequence encoding a foreign product;
   B. ligating said DNA sequence encoding the foreign product into a plasmid, which DNA sequence is operably joined to an RNA polymerase promoter recognized by the RNA polymerase, so as to obtain a recombinant plasmid, wherein replication level and copy number of said recombinant plasmid in the host cell is regulated by an antisense RNA that is polyadenylated by a poly(A) polymerase encoded by the poly(A) polymerase gene that is operably joined to the conditionally-inducible promoter in said host cell;
   C. introducing said recombinant plasmid into said host cell; and
   D. growing said host cell containing said recombinant plasmid that contains said DNA sequence under conditions wherein said conditionally inducible promoter that is operably joined to said poly(A) polymerase gene in said host cell is not induced,
   wherein the host cell is *E. coli*, the antisense RNA molecule is copA or RNAI and the recombinant plasmid is a R1-type or colE1-type plasmid,
   thereby maintaining said recombinant plasmid at low copy in said host cell under said conditions.

2. A method for cloning and stably maintaining a DNA sequence encoding a foreign product in a host cell and subsequently generating a larger amount of said foreign product, said method comprising:

A. providing:
      (1) a host cell for conditional control of copy number of a recombinant plasmid that is introduced into said host cell, wherein said host cell comprises a poly(A) polymerase gene that (a) is operably joined to a conditionally inducible promoter, (b) is located on a chromosome of said host cell, and (c) catalyzes polyadenylation of an antisense RNA molecule that affects initiation of replication from an origin of replication (ori) in said recombinant plasmid wherein the copy number of the recombinant plasmid in the host cell is lower when the poly(A) polymerase gene is uninduced than when the poly(A) polymerase gene is induced, wherein said host cell additionally comprises an RNA polymerase gene operably joined to a conditionally-inducible promoter that is different from the conditionally-inducible promoter to which the poly(A) polymerase gene is operably joined; and
(2) a DNA sequence encoding a foreign product;
B. ligating said DNA sequence encoding the foreign product into a plasmid, which DNA sequence is operably joined to an RNA polymerase promoter recognized by the RNA polymerase, so as to obtain a recombinant plasmid, wherein replication level and copy number of said recombinant plasmid in the host cell is regulated by an antisense RNA that is polyadenylated by a poly(A) polymerase encoded by the poly(A) polymerase gene that is operably joined to the conditionally-inducible promoter in said host cell;
C. introducing said recombinant plasmid into said host cell;
D. growing said host cell containing said recombinant plasmid that contains said DNA sequence under conditions wherein said conditionally inducible promoter that is operably joined to said poly(A) polymerase gene in said host cell is not induced, thereby stably maintaining said recombinant plasmid at low copy in said host cell under said conditions; and
E. contacting the host cell containing the recombinant plasmid with an inducing agent under conditions wherein the conditionally inducible promoter that is joined to the RNA polymerase gene is induced,
wherein the host cell is *E. coli*, the antisense RNA molecule is copA or RNAI and the recombinant plasmid is a R1-type or colE1-type plasmid,
thereby generating a larger amount of the foreign product.

3. A host cell for conditional control of copy number of a recombinant plasmid that contains a DNA sequence encoding a foreign product that is introduced into said host cell for production of the foreign product, wherein said host cell comprises a poly(A) polymerase gene that: (a) is operably joined to a conditionally inducible promoter, (b) is located on a chromosome of said host cell; and (c) catalyzes polyadenylation of an antisense RNA molecule that affects initiation of replication from an origin of replication (ori) in said recombinant plasmid wherein the copy number of the recombinant plasmid in the host cell is lower when the poly(A) polymerase gene is uninduced than when the poly(A) polymerase gene is induced, wherein said host cell additionally comprises an RNA polymerase gene operably joined to a conditionally-inducible promoter that is different from the conditionally-inducible promoter to which the poly(A) polymerase gene is operably joined; and the DNA sequence of the recombinant plasmid is operably joined to a RNA polymerase promoter recognized by the RNA polymerase encoded by the RNA polymerase gene; wherein the host cell is obtained by removing, inactivating or mutating a constitutively-expressed poly(A) polymerase gene and introducing the poly(A) polymerase gene that is operably joined to the conditionally-inducible promoter into the chromosome of the host cell or by operably joining the conditionally-inducible promoter to a poly(A) polymerase gene that is located in a chromosome of the host cell, wherein the host cell is *E. coli*, the antisense RNA molecule is copA or RNAI and the recombinant plasmid is a RI-type or colEI-type plasmid.

* * * * *

UNITED STATES PATENT AND TRADEMARK OFFICE
CERTIFICATE OF CORRECTION

PATENT NO.        : 7,794,971 B1                              Page 1 of 1
APPLICATION NO.   : 10/883459
DATED             : September 14, 2010
INVENTOR(S)       : Darin J. Haskins and Leslie M. Hoffman It is certified that error appears in the above-identified patent and that said Letters Patent is hereby corrected as shown below:

Column 3 line 14 "on could be any on" should be -- ori could be any ori --
    Column 4 line 36 "on" should be -- ori --
    Column 11 line 23 "LAND" should be -- LA/D --

Signed and Sealed this

Sixteenth Day of November, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 69
<212> TYPE: DNA
<213> ORGANISM: Escherichia coli

<400> SEQUENCE: 1
ctccagcagt tccatgcgc gtttaccctg acgacgggac atacgcggat agacggcatg    60
cacgatttg                                                           69

<210> SEQ ID NO 2
<211> LENGTH: 71
<212> TYPE: DNA
<213> ORGANISM: Escherichia coli

<400> SEQUENCE: 2
tccgtaactg cccgcctggt gggtcgccgt ttccgtctgg ctcatggcag gtcgactcta    60
gaggatcccc g                                                        71

<210> SEQ ID NO 3
<211> LENGTH: 30
<212> TYPE: DNA
<213> ORGANISM: Escherichia coli

<400> SEQUENCE: 3
gctatgatta gccggaattc ttttgtcctg                                    30

<210> SEQ ID NO 4
<211> LENGTH: 30
<212> TYPE: DNA
<213> ORGANISM: Escherichia coli

<400> SEQUENCE: 4
ctgcctatgg caagcttcgc cactgtcatg                                    30

<210> SEQ ID NO 5
<211> LENGTH: 23
<212> TYPE: DNA
```

-continued

```
<213> ORGANISM: Escherichia coli

<400> SEQUENCE: 5
cgtcaattgt ctgattcgtt acc                                           23

<210> SEQ ID NO 6
<211> LENGTH: 24
<212> TYPE: DNA
<213> ORGANISM: Escherichia coli

<400> SEQUENCE: 6
gaagcattta tcagggttat tgtc                                          24

<210> SEQ ID NO 7
<211> LENGTH: 19
<212> TYPE: DNA
<213> ORGANISM: Escherichia coli

<400> SEQUENCE: 7
attcaggctg cgcaactgt                                                19

<210> SEQ ID NO 8
<211> LENGTH: 23
<212> TYPE: DNA
<213> ORGANISM: Escherichia coli

<400> SEQUENCE: 8
gtcagtgagc gaggaagcgg aag                                           23
```